(12) United States Patent
Lin et al.

(10) Patent No.: US 10,543,065 B2
(45) Date of Patent: Jan. 28, 2020

(54) INTRAORAL SCANNER, INTRAORAL SCANNING SYSTEM AND METHOD OF CONTROLLING INTRAORAL SCANNER

(71) Applicant: QISDA CORPORATION, Taoyuan (TW)

(72) Inventors: Chi-Cheng Lin, Taoyuan (TW);
Chuang-Wei Wu, Taipei (TW);
Tsung-Hsi Lee, Tainan (TW)

(73) Assignee: Qisda Corporation, Taoyuan (TW)

( * ) Notice: Subject to any disclaimer, the term of this patent is extended or adjusted under 35 U.S.C. 154(b) by 0 days.

(21) Appl. No.: 16/250,954

(22) Filed: Jan. 17, 2019

(65) Prior Publication Data

US 2019/0247162 A1 Aug. 15, 2019

(30) Foreign Application Priority Data

Feb. 12, 2018 (CN) .......................... 2018 1 0144969

(51) Int. Cl.
*A61B 1/24* (2006.01)
*A61C 9/00* (2006.01)
*A61B 5/00* (2006.01)
*A61B 1/247* (2006.01)
*A61B 1/00* (2006.01)

(52) U.S. Cl.
CPC ........ *A61C 9/0053* (2013.01); *A61B 1/00172* (2013.01); *A61B 1/247* (2013.01); *A61B 5/0088* (2013.01); *A61B 5/0062* (2013.01)

(58) Field of Classification Search
None
See application file for complete search history.

(56) References Cited

U.S. PATENT DOCUMENTS

| 6,845,190 B1 * | 1/2005 | Smithwick ........... A61B 1/0008 385/1 |
| 2009/0306506 A1 * | 12/2009 | Heger ..................... A61C 9/00 600/443 |
| 2014/0199649 A1 * | 7/2014 | Apte ..................... A61B 1/045 433/27 |
| 2017/0300119 A1 * | 10/2017 | Wu ......................... A61B 6/145 |
| 2019/0200746 A1 * | 7/2019 | Serval ................ A46B 15/0006 |
| 2019/0269485 A1 * | 9/2019 | Elbaz ................. A61B 1/00016 |

* cited by examiner

*Primary Examiner* — Christopher G Findley (57) ABSTRACT

An intraoral scanner includes an image sensor, a projection module, a motion sensor, a memory unit and a processor. The motion sensor senses three motion variations corresponding to three axes according to a motion state of the intraoral scanner. The memory unit stores three first variation thresholds corresponding to the three axes. The processor determines whether the three motion variations are smaller than or equal to the three first variation thresholds, respectively. When the processor determines that at least one of the three motion variations is smaller than or equal to the three first variation thresholds, the processor enables the image sensor and the projection module. When the processor determines that all of the three motion variations are larger than the three first variation thresholds, the processor disables at least one of the image sensor and the projection module.

15 Claims, 10 Drawing Sheets

INTRAORAL SCANNER, INTRAORAL SCANNING SYSTEM AND METHOD OF CONTROLLING INTRAORAL SCANNER

BACKGROUND OF THE INVENTION

1. Field of the Invention

The invention relates to an intraoral scanner, an intraoral scanning system, and a method of controlling an intraoral scanner and, more particularly, to an intraoral scanner, an intraoral scanning system, and a method of controlling an intraoral scanner capable of reducing power consumption effectively.

2. Description of the Prior Art

An intraoral scanner uses laser to scan tooth rapidly and then transmits the scanned image to a computer, so as to establish a tooth model. In general, an image sensor (namely, an image capturing module such as a micro camera) and a projection module are disposed in a casing of the intraoral scanner. When using the intraoral scanner to scan a tooth, a user has to press a start button on a computer or the intraoral scanner. Then, the image sensor and the projection module start to operate until the user presses a stop button on the computer or the intraoral scanner. However, when the user places the intraoral scanner on a support frame or a table without pressing the stop button, the image sensor and the projection module are still operating continuously, such that power consumption and temperature increase. At this time, the performance of the image sensor and the projection module may decay or fail. Furthermore, the light emitted by the projection module is flashing continuously, such that the patient or the user may feel uncomfortable. Moreover, the computer may receive non-tooth images captured by the image sensor continuously, such that the computer needs to perform addition computation and process.

SUMMARY OF THE INVENTION

An objective of the invention is to provide an intraoral scanner, an intraoral scanning system, and a method of controlling an intraoral scanner capable of reducing power consumption effectively, so as to solve the aforesaid problems.

According to an embodiment of the invention, an intraoral scanner comprises an image sensor, a projection module, a motion sensor, a memory unit, and a processor. The motion sensor senses three motion variations corresponding to three axes according to a motion state of the intraoral scanner. The memory unit stores three first variation thresholds corresponding to the three axes. The processor is electrically connected to the image sensor, the projection module, the motion sensor, and the memory unit. The processor determines whether the three motion variations are smaller than or equal to the three first variation thresholds, respectively. When the processor determines that at least one of the three motion variations is smaller than or equal to the three first variation thresholds, the processor enables the image sensor and the projection module. When the processor determines that all of the three motion variations are larger than the three first variation thresholds, the processor disables at least one of the image sensor and the projection module.

According to another embodiment of the invention, an intraoral scanning system comprises a host device and an intraoral scanner. The host device stores three first variation thresholds corresponding to three axes. The intraoral scanner communicates with the host device. The intraoral scanner comprises an image sensor, a projection module, a motion sensor, and a processor. The motion sensor senses three motion variations corresponding to the three axes according to a motion state of the intraoral scanner. The processor is electrically connected to the image sensor, the projection module, and the motion sensor. The host device determines whether the three motion variations are smaller than or equal to the three first variation thresholds, respectively. When the host device determines that at least one of the three motion variations is smaller than or equal to the three first variation thresholds, the host device controls the processor to enable the image sensor and the projection module. When the host device determines that all of the three motion variations are larger than the three first variation thresholds, the host device controls the processor to disable at least one of the image sensor and the projection module.

According to another embodiment of the invention, a method of controlling an intraoral scanner comprises steps of sensing, by the motion sensor, three motion variations corresponding to three axes according to a motion state of the intraoral scanner; determining whether the three motion variations are smaller than or equal to three first variation thresholds corresponding to the three axes, respectively; when determining that at least one of the three motion variations is smaller than or equal to the three first variation thresholds, enabling the image sensor and the projection module; and when determining that all of the three motion variations are larger than the three first variation thresholds, disabling at least one of the image sensor and the projection module.

As mentioned in the above, the invention disposes a motion sensor in the intraoral scanner and the motion sensor senses three motion variations corresponding to three axes according to a motion state of the intraoral scanner. When at least one of the three motion variations is smaller than or equal to the three first variation thresholds, it means that the intraoral scanner is in an operation state, i.e. a user is using the intraoral scanner to scan a tooth. At this time, the image sensor and the projection module of the intraoral scanner will be enabled, such that the image sensor and the projection module can operate normally. When all of the three motion variations are larger than the three first variation thresholds, it means that the intraoral scanner is in an idle state. At this time, at least one of the image sensor and the projection module will be disabled, such that at least one of the image sensor and the projection module stop operating. Accordingly, the invention can reduce power consumption and avoid temperature rise effectively while the intraoral scanner is in an idle state.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
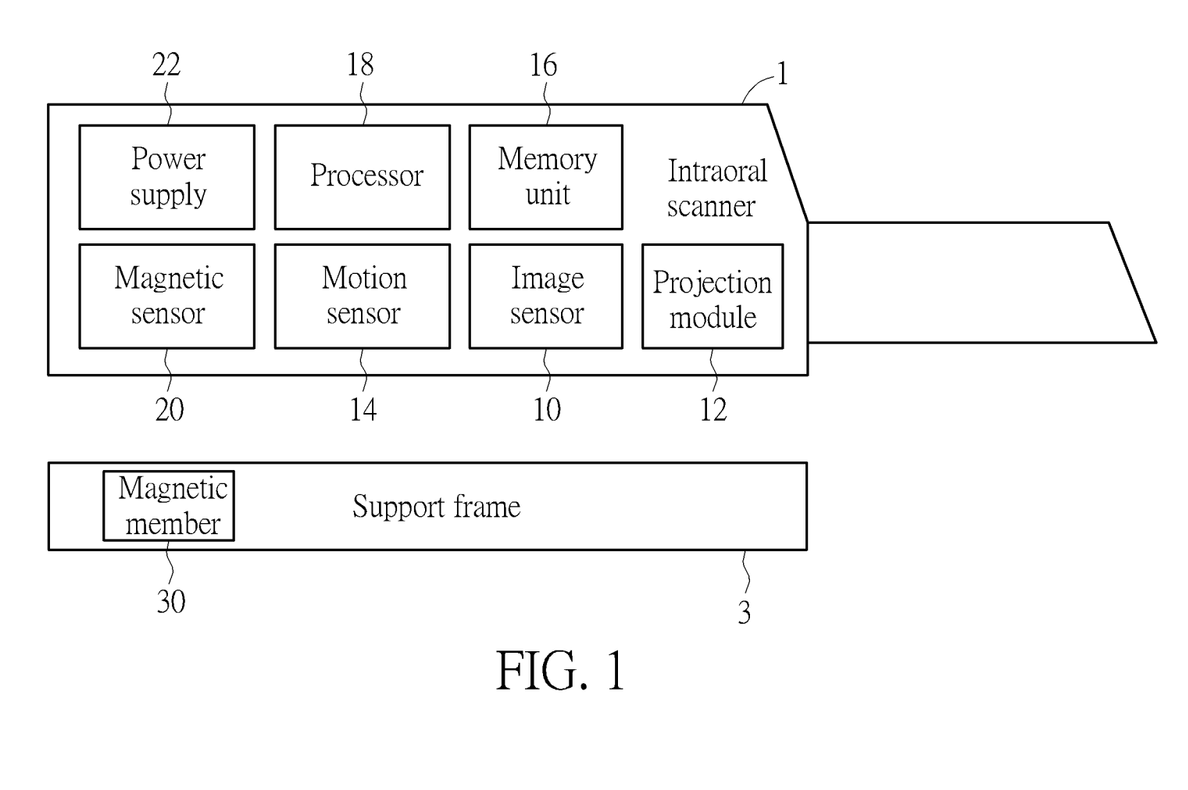
FIG. 1 is a functional block diagram illustrating an intraoral scanner according to an embodiment of the invention.
Figure 2:
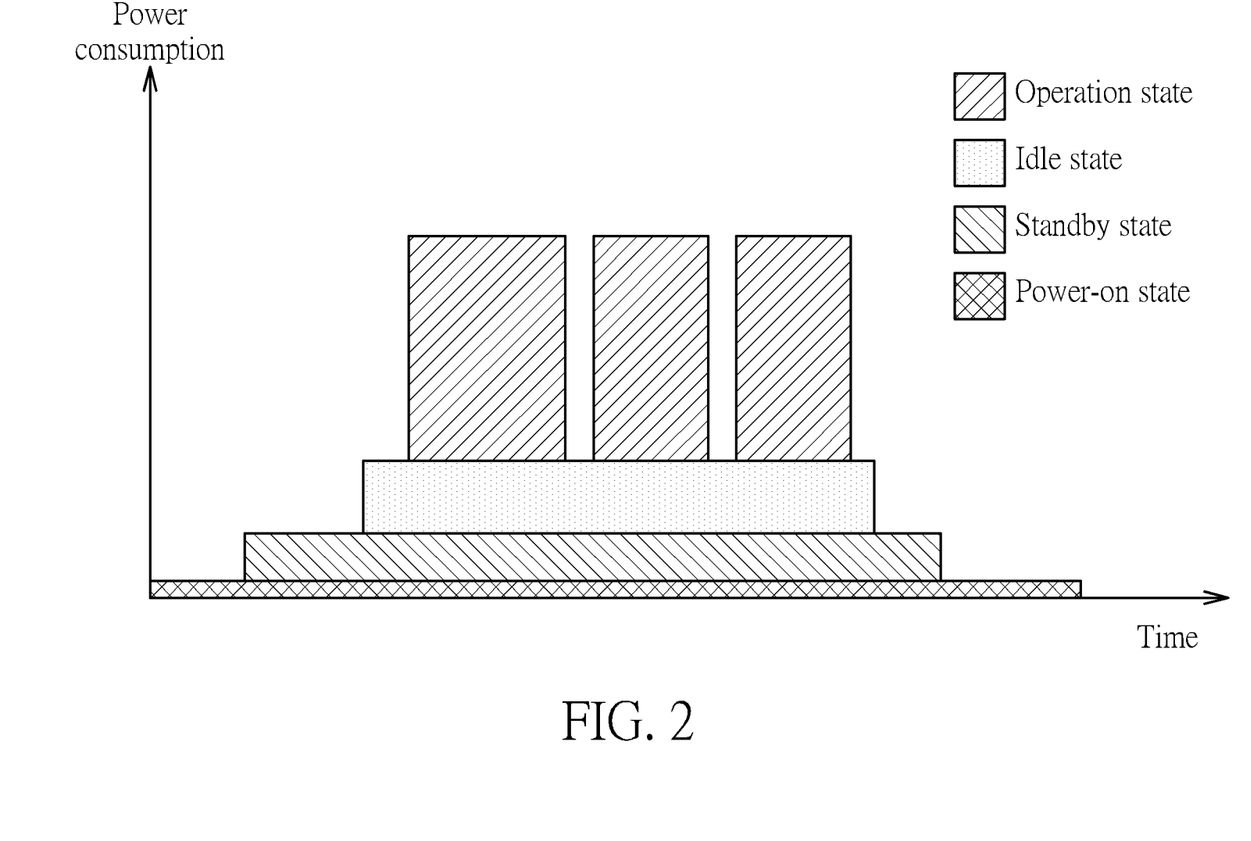
FIG. 2 is a schematic diagram illustrating power consumption of the intraoral scanner in different states.
Figure 3:
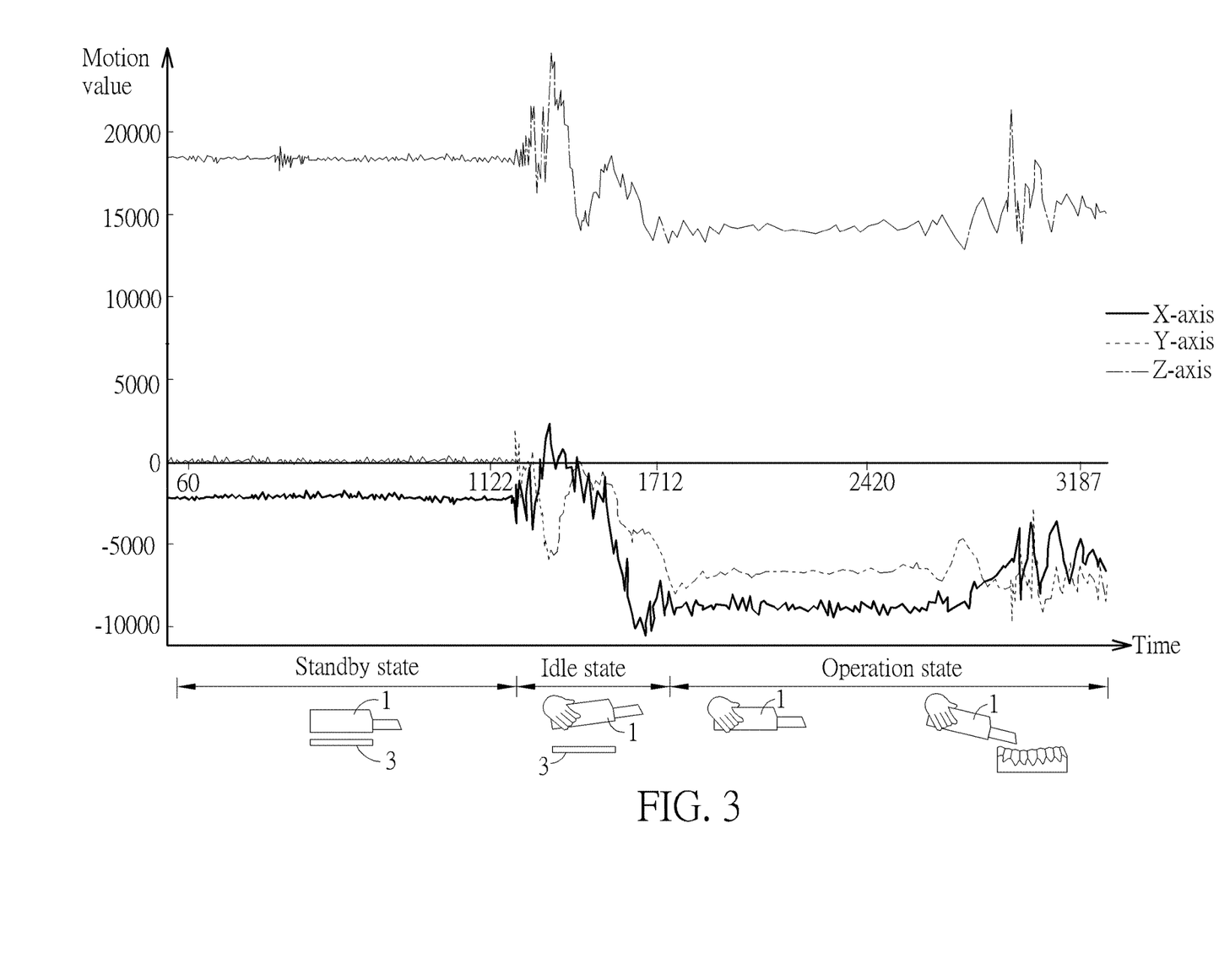
FIG. 3 is a curve diagram illustrating three-axis motion state of the intraoral scanner sensed by the motion sensor.

Referring to FIGS. 1 to 3, FIG. 1 is a functional block diagram illustrating an intraoral scanner 1 according to an embodiment of the invention, FIG. 2 is a schematic diagram illustrating power consumption of the intraoral scanner 1 in different states, and FIG. 3 is a curve diagram illustrating three-axis motion state of the intraoral scanner 1 sensed by the motion sensor 14.

As shown in FIG. 1, the intraoral scanner 1 comprises an image sensor 10, a projection module 12, a motion sensor 14, a memory unit 16, a processor 18, a magnetic sensor 20, and a power supply 22, wherein the processor 18 is electrically connected to the image sensor 10, the projection module 12, the motion sensor 14, the memory unit 16, the magnetic sensor 20, and the power supply 22. The power supply 22 is configured to supply power to the image sensor 10, the projection module 12, the motion sensor 14, the memory unit 16, the processor 18, the magnetic sensor 20, and other electronic components.

In practical applications, the projection module 12 may be a digital light processing (DLP) module or other projection modules to project a predetermined image to the three-dimensional object such as teeth, so as to form a constructed image on a surface of the three-dimensional object. The image sensor 10 may be an image capturing module, e.g., a charge-coupled device (CCD) sensor or a complementary metal-oxide semiconductor (CMOS) sensor, to capture the constructed image formed on the surface of the three-dimensional object such as teeth. The motion sensor 14 may be a G sensor, a gyro, or a combination thereof; the memory unit 16 may be a memory or other data storage devices; the processor 18 may be a processor or a controller with data calculating/processing function; the magnetic sensor 20 may a Hall sensor; and the power supply 22 may be a battery. In general, the intraoral scanner 1 may be further equipped with some necessary hardware or software components for specific purposes, such as a circuit board, applications, a communication module, etc., and it depends on practical applications.

In general, there is a power button (not shown) disposed on the intraoral scanner 1. When a user presses the power button, the processor 18 is woken up and the magnetic sensor 20 is enabled. At this time, the image sensor 10, the projection module 12, and the motion sensor 14 are disabled without power consumption. Accordingly, as shown in FIG. 2, when the intraoral scanner 1 is in a power-on state, the power consumption is very low.

Since the magnetic sensor 20 is enabled as the intraoral scanner 1 is powered on, the magnetic sensor 20 can operate normally. In this embodiment, the intraoral scanner 1 is adapted to be disposed on a support frame 3. The support frame 3 comprises a magnetic member 30 and the memory unit 16 stores a voltage threshold, wherein the voltage threshold may be set according to practical applications. The magnetic sensor 20 is configured to sense a magnetic flux of the magnetic member 30 to generate a sensing voltage. Then, the processor 18 determines whether the sensing voltage is larger than or equal to the voltage threshold. The invention may determine whether the intraoral scanner 1 is placed on the support frame 3 according to the comparison result of the sensing voltage and the voltage threshold.

When the processor determines that the sensing voltage is larger than or equal to the voltage threshold, it means that the intraoral scanner 1 is placed on the support frame 3, i.e. the intraoral scanner 1 is in a standby state. At this time, the processor 18 will enable the motion sensor 14, such that the motion sensor 14 can operate normally. Accordingly, as shown in FIG. 2, when the intraoral scanner 1 is in a standby state, the power consumption will increase slightly.

When the processor determines that the sensing voltage is smaller than the voltage threshold, it means that the intraoral scanner 1 is removed from the support frame 3, i.e. the intraoral scanner 1 is in an idle state. At this time, the processor 18 will control the power supply 22 to supply power to the image sensor 10 and the projection module 12. Accordingly, as shown in FIG. 2, when the intraoral scanner 1 is in an idle state, the power consumption will increase continuously.

Since the motion sensor 14 is enabled as the intraoral scanner 1 is in a standby state, the motion sensor 14 can operate normally. The motion sensor 14 is configured to sense three motion variations corresponding to three axes according to a motion state of the intraoral scanner 1, wherein the aforesaid three axes may be three axes X, Y, Z in a three-dimensional coordinate system and the motion sensor 14 may be a three-axis sensor. As shown in FIG. 3, the motion sensor 14 may sense three-axis motion state of the intraoral scanner 1 in different states, wherein the standby state represents that the intraoral scanner 1 is placed on the support frame 3, the idle state represents that the intraoral scanner 1 is removed from the support frame 3, and the operation state represents that the intraoral scanner 1 moves to an oral cavity and starts to scan a tooth. Furthermore, the memory unit 16 stores three first variation thresholds corresponding to the three axes, wherein the three first variation thresholds may be set according to practical applications.

The processor 18 determines whether the three motion variations of the intraoral scanner 1 are smaller than or equal to the three first variation thresholds, respectively, so as to determine that the intraoral scanner 1 is in an operation state or in an idle state. When the processor 18 determines that at least one of the three motion variations is smaller than or equal to the three first variation thresholds, it means that the intraoral scanner 1 is moving stably, i.e. the intraoral scanner 1 is in an operation state. At this time, the processor 18 will enable the image sensor 10 and the projection module 12, such that the image sensor 10 and the projection module 12 can operate normally. Accordingly, as shown in FIG. 2, when the intraoral scanner 1 is in an operation state, the power consumption is largest.

When the processor 18 determines that all of the three motion variations of the intraoral scanner 1 are larger than the three first variation thresholds, it means that the intraoral scanner 1 is shaking violently, i.e. the intraoral scanner 1 is in an idle state. At this time, the processor 18 will disable at least one of the image sensor 10 and the projection module 12, such that at least one of the image sensor 10 and the projection module 12 stops operating. Accordingly, as shown in FIG. 2, the power consumption of the intraoral scanner 1 in an idle state is smaller than the power consumption of the intraoral scanner 1 in an operation state.

The invention may take a difference between a maximum motion value and a minimum motion value sensed by the motion sensor 14 within a time period (three seconds, five seconds, etc.) to be the aforesaid motion variation. It is assumed that the first variation threshold corresponding to X-axis is equal to 100. If the difference between the maximum motion value and the minimum motion value corresponding to X-axis sensed by the motion sensor 14 within a time period is equal to 90, the motion variation corresponding to X-axis is smaller than the first variation threshold corresponding to X-axis. On the other hand, if the difference between the maximum motion value and the minimum motion value corresponding to X-axis sensed by the motion sensor 14 within a time period is equal to 120, the motion variation corresponding to X-axis is larger than the first variation threshold corresponding to X-axis. The determination for Y-axis and Z-axis is identical to the determination for X-axis, so it will not be depicted herein again.

Furthermore, when the processor 18 determines that the sensing voltage of the magnetic sensor 20 is larger than or equal to the voltage threshold, the processor 18 may set three second variation thresholds corresponding to the three axes according to the three motion variations sensed by the motion sensor 14 and stores the three second variation thresholds in the memory unit 16, wherein the three second variation thresholds are smaller than the three first variation thresholds, respectively. When the processor 18 determines that the sensing voltage of the magnetic sensor 20 is smaller than the voltage threshold and all of the three motion variations are smaller than or equal to the three second variation thresholds, it means that the intraoral scanner 1 is removed from the support frame 3 and placed on a table or other planes. At this time, the intraoral scanner 1 should be still in a standby state rather than an idle state. Accordingly, the processor 18 may control the power supply 22 to stop supplying power to the image sensor 10 and the projection module 12, so as to reduce power consumption.

The invention may set the aforesaid second variation threshold by adding a tolerance to the motion variation within a time period (three seconds, five seconds, etc.). It is assumed that the tolerance is equal to 10 and the motion variation corresponding to X-axis within a time period is equal to 20. Then, the second variation threshold corresponding to X-axis may be set to be 30. The setting of the second variation threshold for Y-axis and Z-axis is identical to the setting of the second variation threshold for X-axis, so it will not be depicted herein again. Still further, the second variation threshold may be set while the intraoral scanner 1 is powered on first time, but is not so limited.

Moreover, the invention may further utilize the blur of an image sequence sensed by the image sensor 10 to determine whether the intraoral scanner 1 is in an idle state. In this embodiment, the memory unit 16 stores a blur threshold, wherein the blur threshold may be set according to practical applications. When the image sensor 10 senses an image sequence, the processor 18 determines whether a blur of at least one image of the image sequence is larger than or equal to the blur threshold. When the processor 18 determines that the blur of the at least one image is larger than or equal to the blur threshold, it means that the image sequence is not obtained by scanning a tooth, i.e. the intraoral scanner 1 is in an idle state. At this time, the processor 18 will disable at least one of the image sensor 10 and the projection module 12, such that at least one of the image sensor 10 and the projection module 12 stops operating, so as to reduce power consumption. When the processor 18 determines that the blur of the at least one image is smaller than the blur threshold, it means that the image sequence is obtained by scanning a tooth, i.e. the intraoral scanner 1 is in an operation state. At this time, the image sensor 10 and the projection module 12 can operate normally and continuously.

Figure 4:
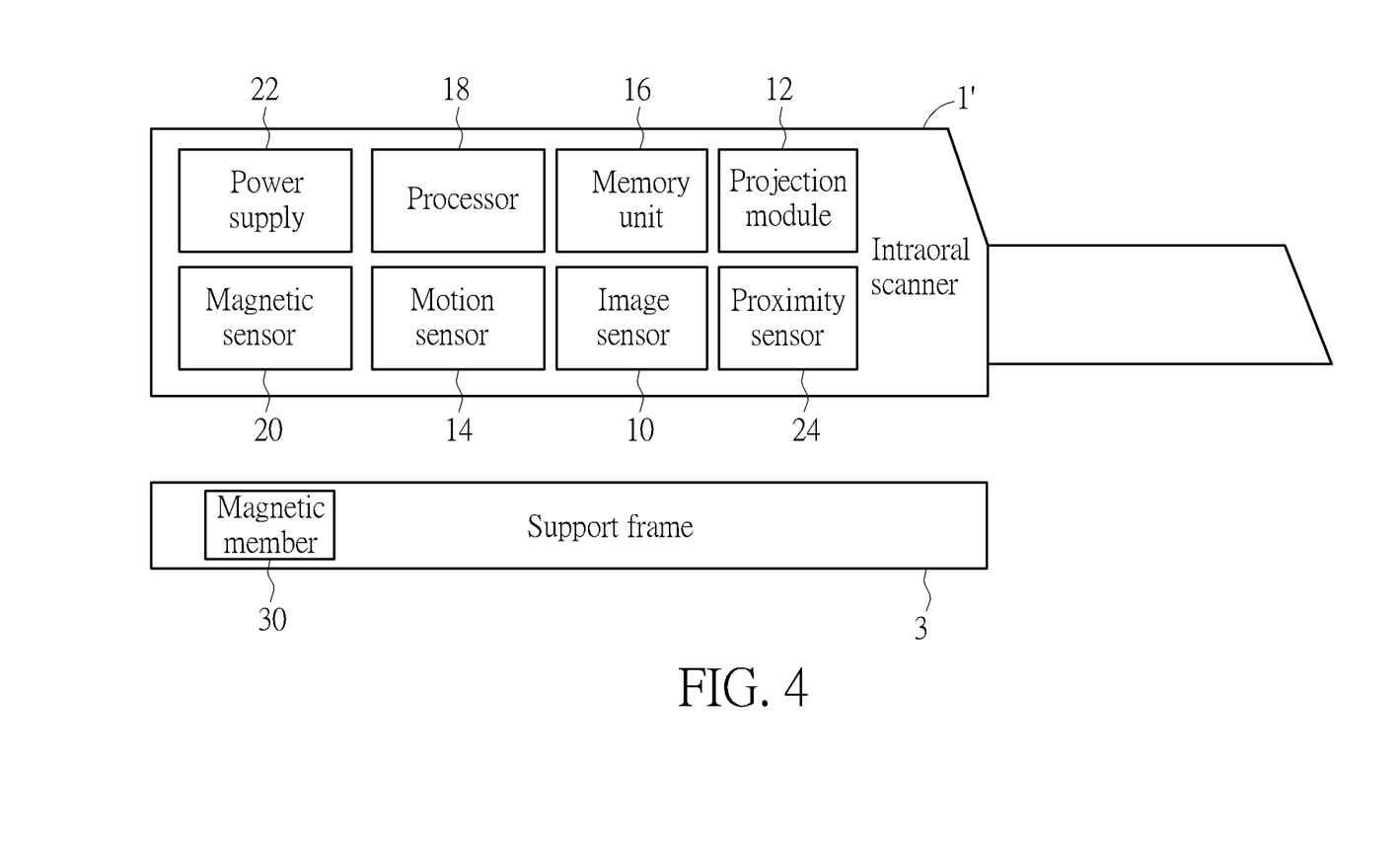
FIG. 4 is a functional block diagram illustrating an intraoral scanner according to another embodiment of the invention.
Figure 5:
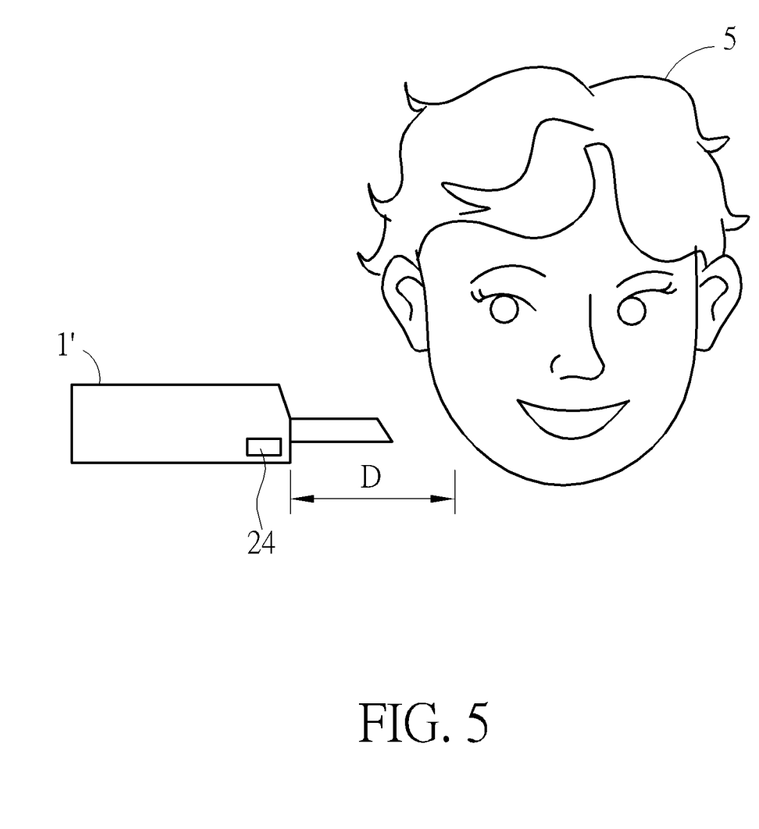
FIG. 5 is a schematic diagram illustrating the intraoral scanner and an object.

Referring to FIGS. 4 and 5, FIG. 4 is a functional block diagram illustrating an intraoral scanner 1' according to another embodiment of the invention and FIG. 5 is a schematic diagram illustrating the intraoral scanner 1' and an object 5. The main difference between the intraoral scanner 1' and the aforesaid intraoral scanner 1 is that the intraoral scanner 1' further comprises a proximity sensor 24, wherein the processor 18 is electrically connected to the proximity sensor 24, as shown in FIG. 4. Furthermore, the memory unit 16 stores a distance threshold, wherein the distance threshold may be set according to practical applications. The proximity sensor 24 is configured to sense a current distance D between the intraoral scanner 1' and an object 5 (e.g., a head of a patient), as shown in FIG. 5. Then, the processor 18 determines whether the current distance D is smaller than or equal to the distance threshold. The invention may determine that the intraoral scanner 1' is in an operation state or in an idle state according to the comparison result of the current distance and the distance threshold.

When the processor 18 determines that the current distance D is smaller than or equal to the distance threshold, it means that the intraoral scanner 1' moves to an oral cavity and starts to scan a tooth, i.e. the intraoral scanner 1' is in an operation state. At this time, the processor 18 will enable the image sensor 10 and the projection module 12, such that the image sensor 10 and the projection module 12 can operate normally. On the other hand, when the processor 18 determines that the current distance D is larger than the distance threshold, it means that the intraoral scanner 1' has moved away from the oral cavity, i.e. the intraoral scanner 1' is in an idle state. At this time, the processor 18 will disable at least one of the image sensor 10 and the projection module 12, such that at least one of the image sensor 10 and the projection module 12 stops operating, so as to reduce power consumption.

Figure 6:
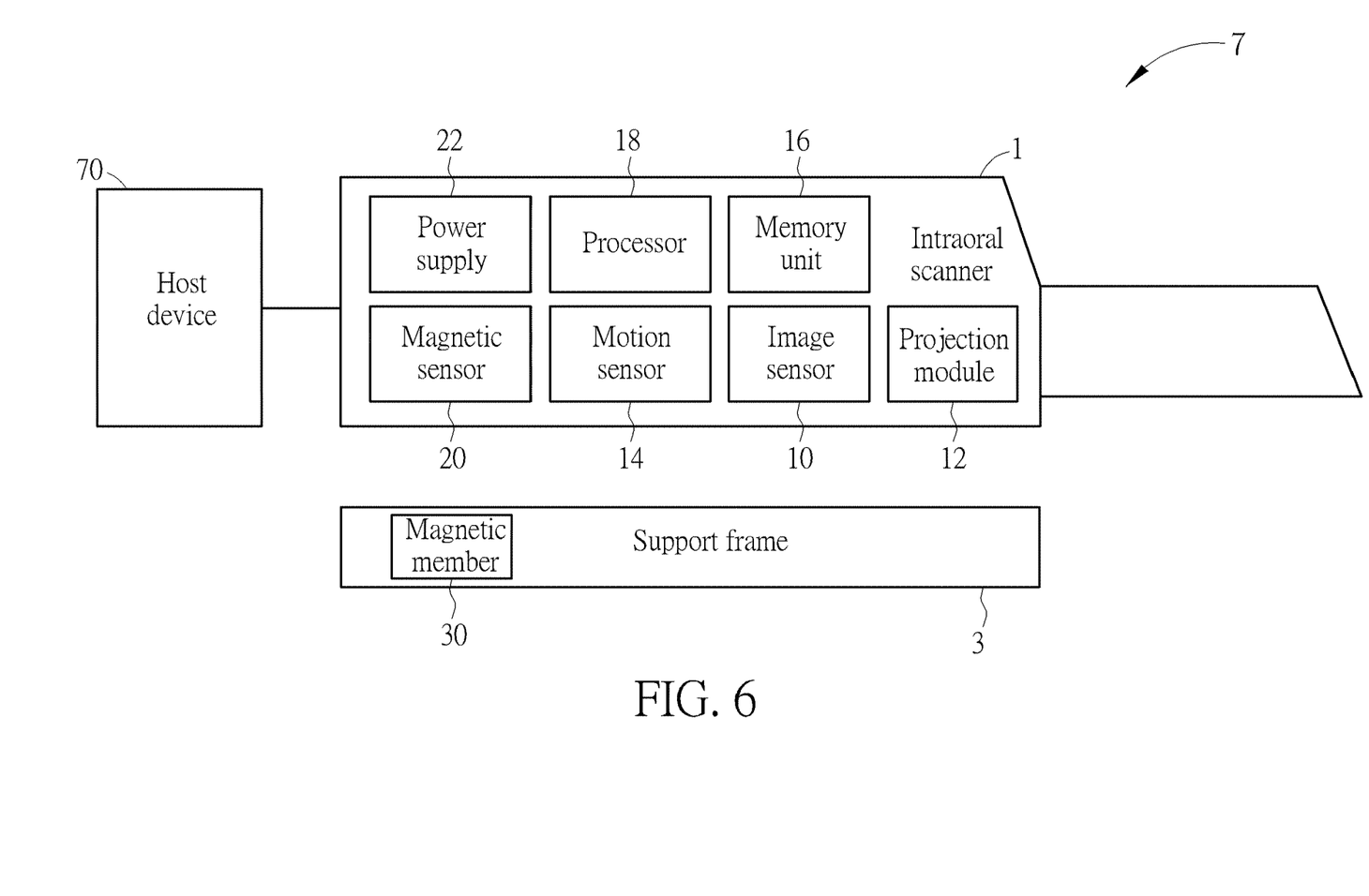
FIG. 6 is a functional block diagram illustrating an intraoral scanning system according to another embodiment of the invention.

Referring to FIG. 6, FIG. 6 is a functional block diagram illustrating an intraoral scanning system 7 according to another embodiment of the invention. As shown in FIG. 6, the intraoral scanning system 7 comprises a host device 70, the aforesaid intraoral scanner 1, and the aforesaid support frame 3. The intraoral scanner 1 may communicate with the host device 70 through wired or wireless connection. In practical applications, the host device 70 may be a computer.

In this embodiment, the host device 70 stores the aforesaid three first variation thresholds corresponding to the three axes. Accordingly, in the intraoral scanning system 7, the host device 70 may determine whether the three motion variations of the intraoral scanner 1 are smaller than or equal to the three first variation thresholds, respectively. When the host device 70 determines that at least one of the three motion variations is smaller than or equal to the three first variation thresholds, the host device 70 will control the processor 18 of the intraoral scanner 1 to enable the image sensor 10 and the projection module 12. On the other hand, when the host device 70 determines that all of the three motion variations are larger than the three first variation thresholds, the host device 70 will control the processor 18 of the intraoral scanner 1 to disable at least one of the image sensor 10 and the projection module 12. It should be noted that the detailed principle has been depicted in the above, so it will not be depicted herein again.

In this embodiment, the host device 70 may store the aforesaid voltage threshold. Accordingly, in the intraoral scanning system 7, the host device 70 may determine whether the sensing voltage of the magnetic sensor 20 is larger than or equal to the voltage threshold. When the host device 70 determines that the sensing voltage of the magnetic sensor 20 is larger than or equal to the voltage threshold, the host device 70 will control the processor 18 of the intraoral scanner 1 to enable the motion sensor 14. On the other hand, when the host device 70 determines that the sensing voltage of the magnetic sensor 20 is smaller than the voltage threshold, the host device 70 will control the processor 18 of the intraoral scanner 1 to control the power supply 22 to supply power to the image sensor 10 and the projection module 12. It should be noted that the detailed principle has been depicted in the above, so it will not be depicted herein again.

Furthermore, when the host device 70 determines that the sensing voltage of the magnetic sensor 20 is larger than or equal to the voltage threshold, the host device 70 may set the aforesaid three second variation thresholds corresponding to the three axes according to the three motion variations of the intraoral scanner 1 and stores the three second variation thresholds. When the host device 70 determines that the sensing voltage of the magnetic sensor 20 is smaller than the voltage threshold and all of the three motion variations of the intraoral scanner 1 are smaller than or equal to the three second variation thresholds, the host device 70 will control the processor 18 of the intraoral scanner 1 to control the power supply 22 to stop supplying power to the image sensor 10 and the projection module 12. It should be noted that the detailed principle has been depicted in the above, so it will not be depicted herein again.

In this embodiment, the host device 70 may store a blur threshold. Accordingly, in the intraoral scanning system 7, the host device 70 may determine whether a blur of at least one image of the image sequence is larger than or equal to the blur threshold. When the host device 70 determines that the blur of the at least one image is larger than or equal to the blur threshold, the host device 70 will control the processor 18 of the intraoral scanner 1 to disable at least one of the image sensor and the projection module. When the host device 70 determines that the blur of the at least one image is smaller than the blur threshold, the image sensor 10 and the projection module 12 can operate normally and continuously. It should be noted that the detailed principle has been depicted in the above, so it will not be depicted herein again.

In another embodiment, the intraoral scanner 1 of the intraoral scanning system 7 may be replaced by the intraoral scanner 1' shown in FIG. 4. At this time, the host device 70 may store the aforesaid distance threshold. Accordingly, in the intraoral scanning system 7, the host device 70 may determine whether the aforesaid current distance D is smaller than or equal to the distance threshold. When the host device 70 determines that the current distance D is smaller than or equal to the distance threshold, the host device 70 will control the processor 18 of the intraoral scanner 1' to enable the image sensor 10 and the projection module 12. On the other hand, when the host device 70 determines that the current distance D is larger than the distance threshold exceeding a predetermined time period, the host device 70 will control the processor 18 of the intraoral scanner 1' to disable at least one of the image sensor 10 and the projection module 12. It should be noted that the detailed principle has been depicted in the above, so it will not be depicted herein again.

Figure 7:
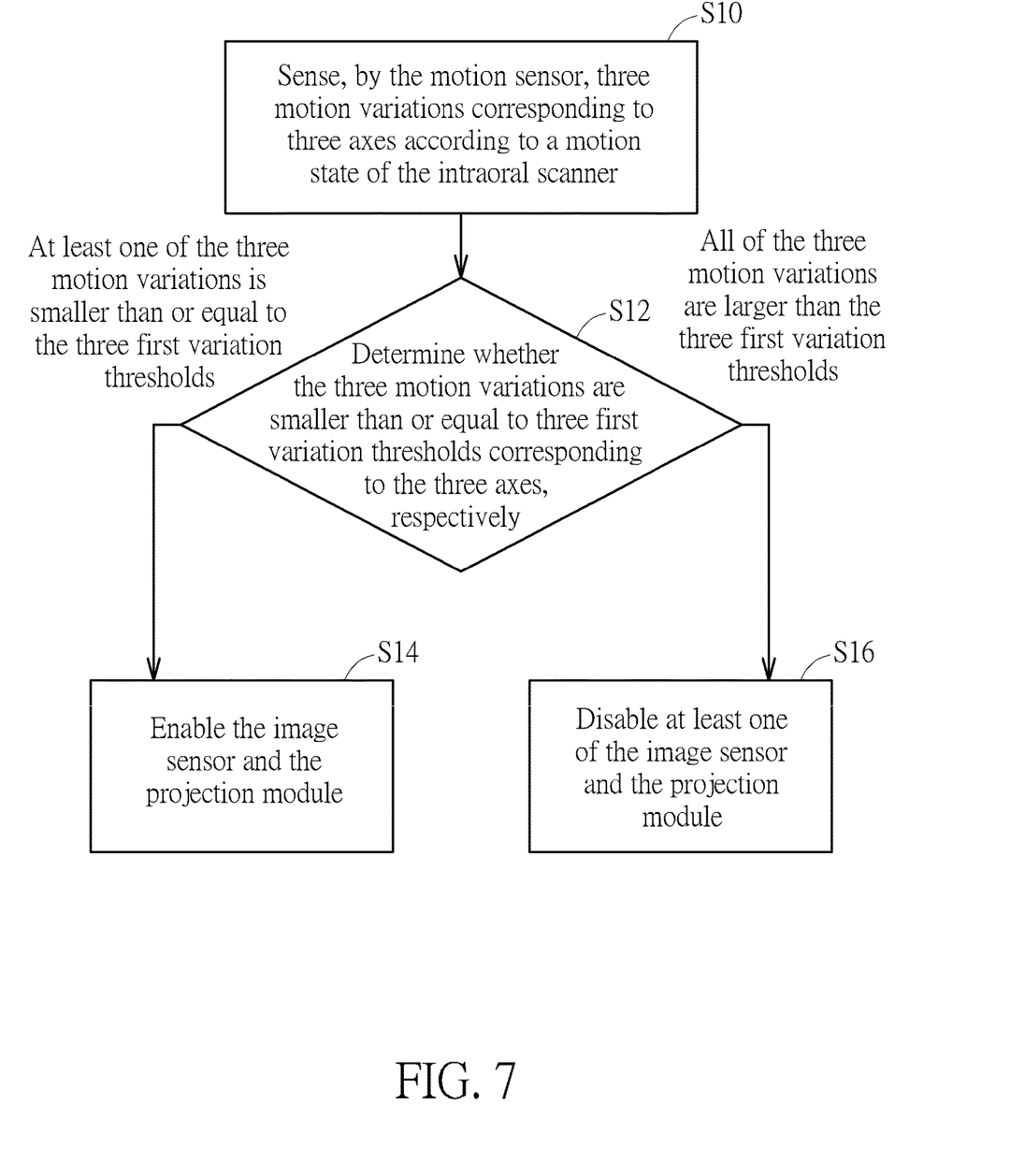
FIG. 7 is a flowchart illustrating a method of controlling an intraoral scanner according to an embodiment of the invention.

Referring to FIG. 7, FIG. 7 is a flowchart illustrating a method of controlling an intraoral scanner according to an embodiment of the invention. The method of controlling the intraoral scanner shown in FIG. 7 may be implemented by the aforesaid intraoral scanners 1, 1' or intraoral scanning system 7. First, step S10 is performed to sense, by the motion sensor 14, three motion variations corresponding to three axes according to a motion state of the intraoral scanner 1, 1'. Then, step S12 is performed to determine whether the three motion variations are smaller than or equal to three first variation thresholds corresponding to the three axes, respectively. When determining that at least one of the three motion variations is smaller than or equal to the three first variation thresholds, step S14 is performed to enable the image sensor 10 and the projection module 12. When determining that all of the three motion variations are larger than the three first variation thresholds, step S16 is performed to disable at least one of the image sensor 10 and the projection module 12.

Figure 8:
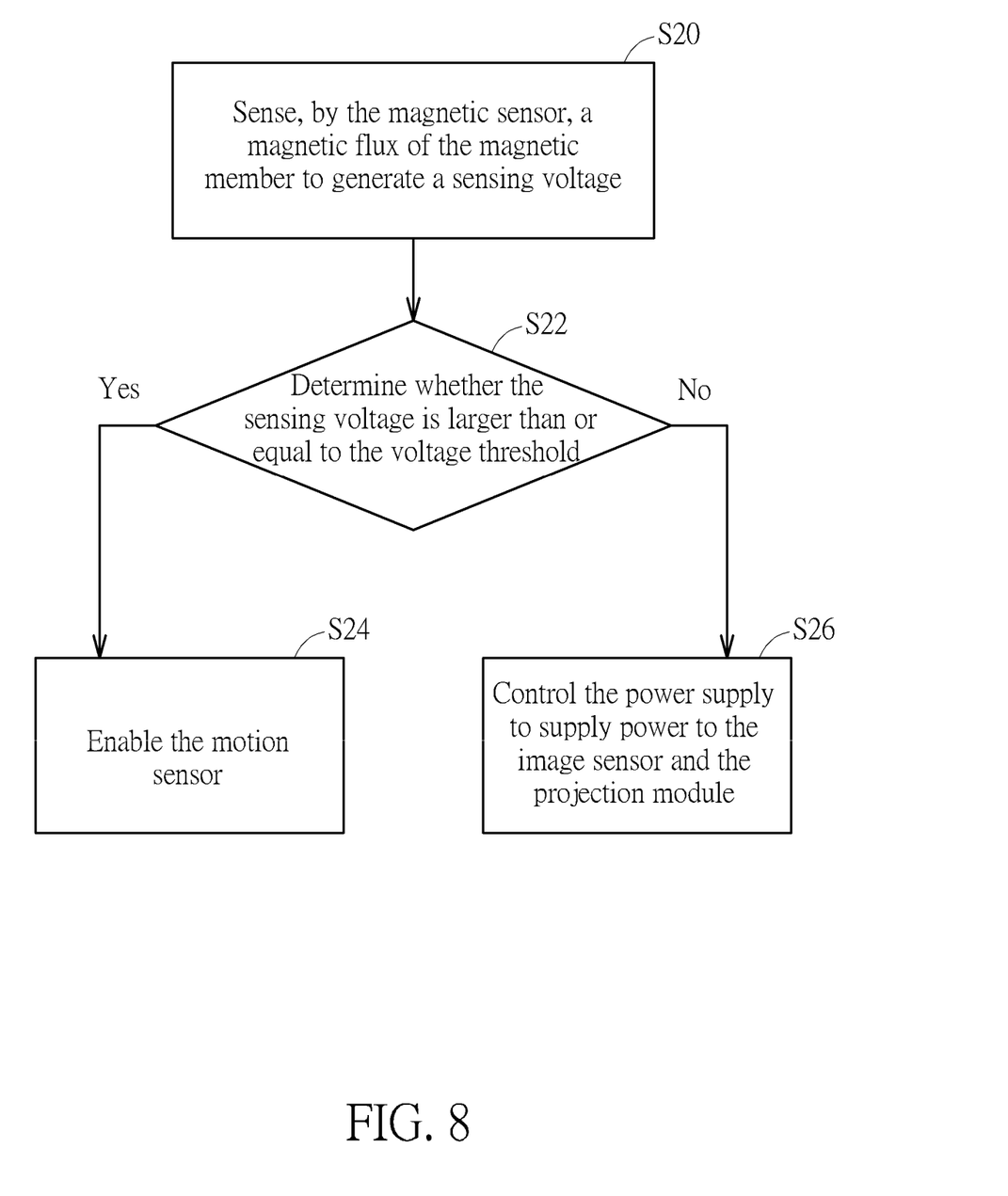
FIG. 8 is a flowchart illustrating a method of controlling an intraoral scanner according to another embodiment of the invention.

Referring to FIG. 8, FIG. 8 is a flowchart illustrating a method of controlling an intraoral scanner according to another embodiment of the invention. The method of controlling the intraoral scanner shown in FIG. 8 may be implemented by the aforesaid intraoral scanners 1, 1' or intraoral scanning system 7. First, step S20 is performed to sense, by the magnetic sensor 20, a magnetic flux of the magnetic member 30 to generate a sensing voltage. Then, step S22 is performed to determine whether the sensing voltage is larger than or equal to the voltage threshold. When determining that the sensing voltage is larger than or equal to the voltage threshold, step S24 is performed to enable the motion sensor 14. When determining that the sensing voltage is smaller than the voltage threshold, step S26 is performed to control the power supply 22 to supply power to the image sensor 10 and the projection module 12. In this embodiment, when determining that the sensing voltage is larger than or equal to the voltage threshold, the method may set three second variation thresholds corresponding to the three axes according to the three motion variations, wherein the three second variation thresholds are smaller than the three first variation thresholds, respectively. When determining that the sensing voltage is smaller than the voltage threshold and all of the three motion variations are smaller than or equal to the three second variation thresholds, the method may control the power supply 22 to stop supplying power to the image sensor 10 and the projection module 12.

Figure 9:
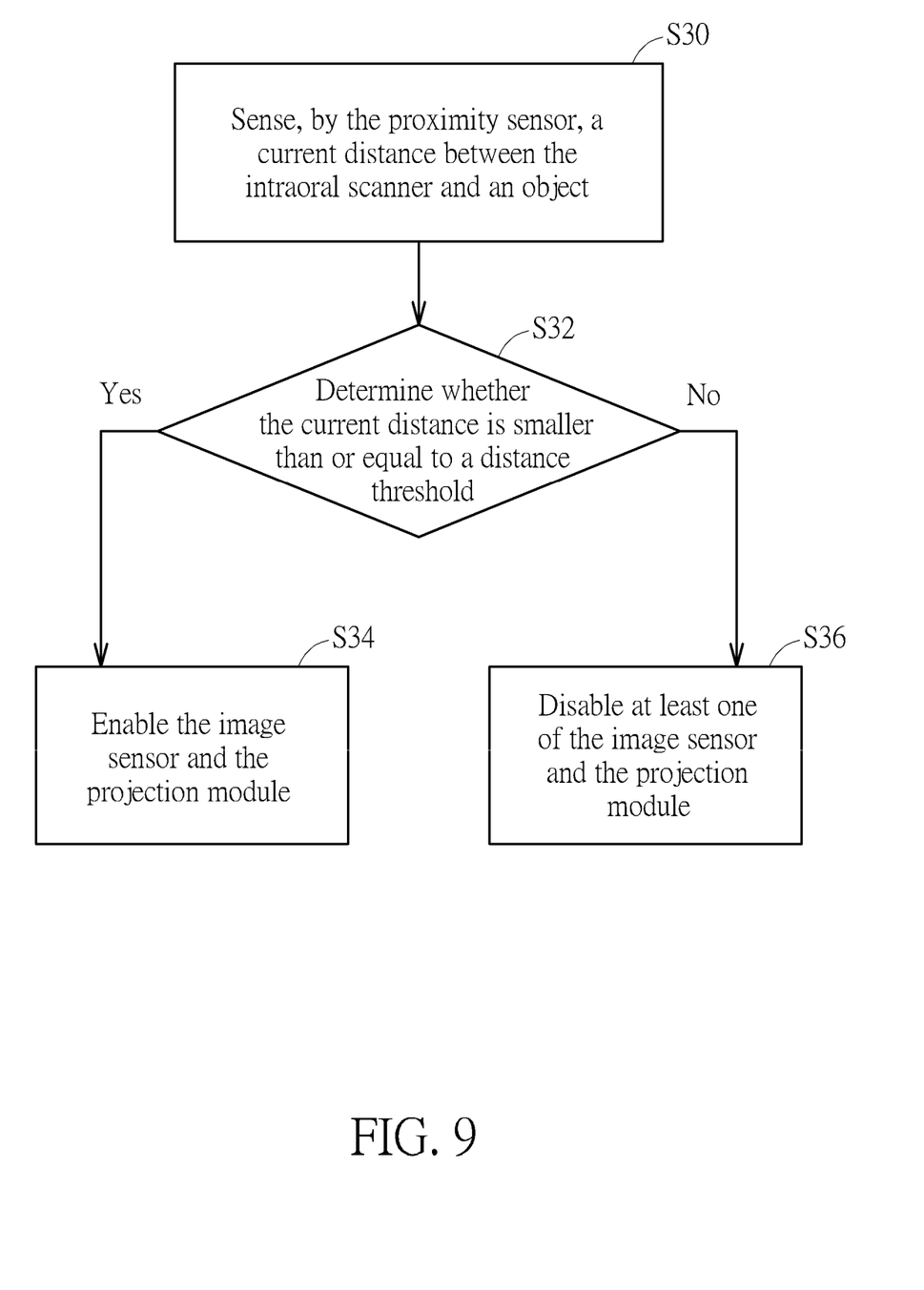
FIG. 9 is a flowchart illustrating a method of controlling an intraoral scanner according to another embodiment of the invention.

Referring to FIG. 9, FIG. 9 is a flowchart illustrating a method of controlling an intraoral scanner according to another embodiment of the invention. The method of controlling the intraoral scanner shown in FIG. 9 may be implemented by the aforesaid intraoral scanner 1' or intraoral scanning system 7. First, step S30 is performed to sense, by the proximity sensor 24, a current distance D between the intraoral scanner 1' and an object 5. Then, step S32 is performed to determine whether the current distance D is smaller than or equal to a distance threshold. When determining that the current distance D is smaller than or equal to the distance threshold, step S34 is performed to enable the image sensor 10 and the projection module 12. When determining that the current distance D is larger than the distance threshold exceeding a predetermined time period, step S36 is performed to disable at least one of the image sensor 10 and the projection module 12.

Figure 10:
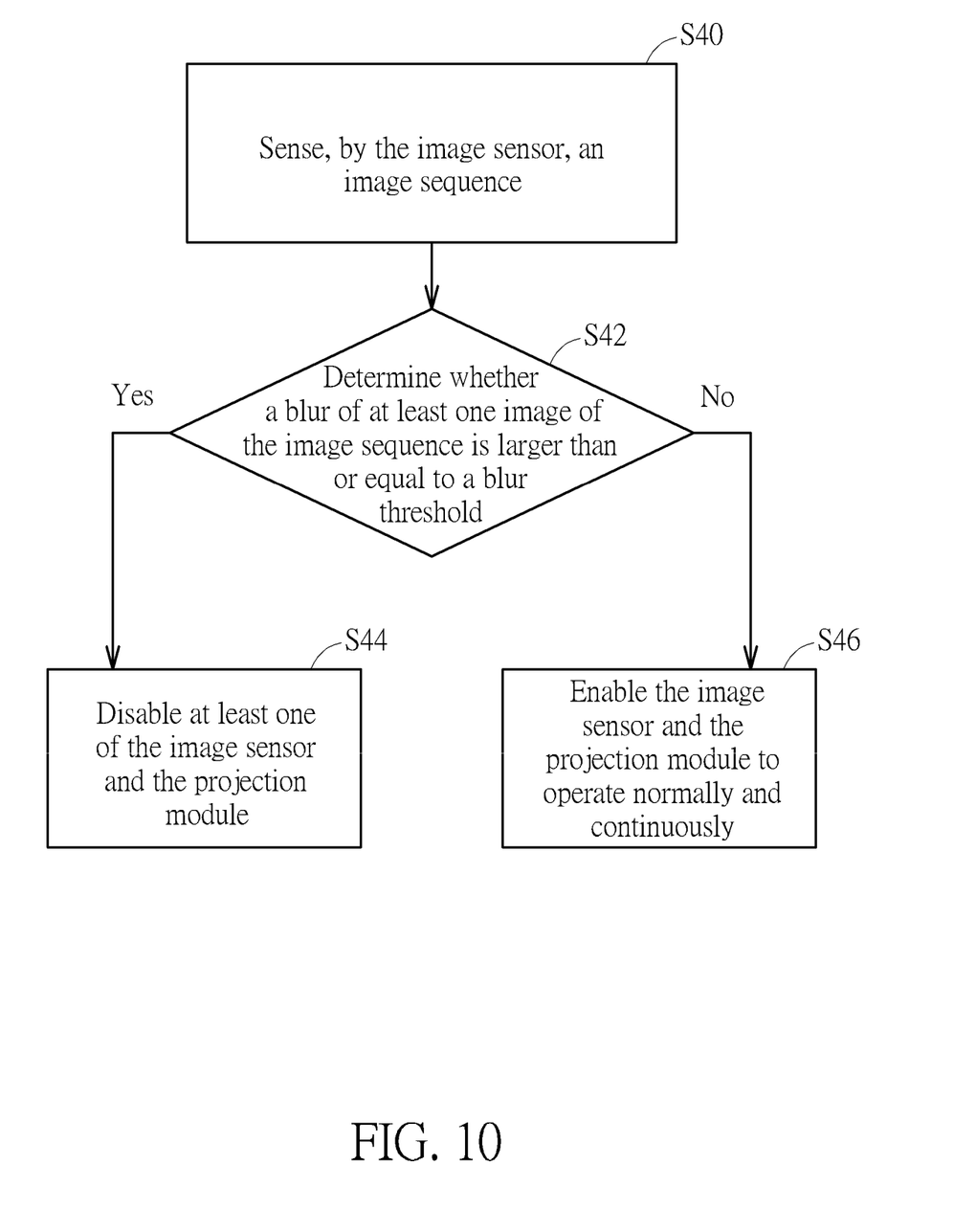
FIG. 10 is a flowchart illustrating a method of controlling an intraoral scanner according to another embodiment of the invention.

Referring to FIG. 10, FIG. 10 is a flowchart illustrating a method of controlling an intraoral scanner according to another embodiment of the invention. The method of controlling the intraoral scanner shown in FIG. 10 may be implemented by the aforesaid intraoral scanners 1, 1' or intraoral scanning system 7. First, step S40 is performed to sense, by the image sensor 10, an image sequence. Then, step S42 is performed to determine whether a blur of at least one image of the image sequence is larger than or equal to a blur threshold. When determining that the blur of the at least one image is larger than or equal to the blur threshold, step S44 is performed to disable at least one of the image sensor 10 and the projection module 12. When determining that the blur of the at least one image is smaller than the blur threshold, step S46 is performed to enable the image sensor 10 and the projection module 12 to operate normally and continuously.

It should be noted that the detailed embodiments of the method of controlling the intraoral scanner of the invention are mentioned in the above and those will not be depicted herein again. Furthermore, each part or function of the control logic of the method of controlling the intraoral scanner shown in FIGS. 7 to 10 may be implemented by software, hardware or the combination thereof.

As mentioned in the above, the invention disposes a motion sensor in the intraoral scanner and the motion sensor senses three motion variations corresponding to three axes according to a motion state of the intraoral scanner. When at least one of the three motion variations is smaller than or equal to the three first variation thresholds, it means that the intraoral scanner is in an operation state, i.e. a user is using the intraoral scanner to scan a tooth. At this time, the image sensor and the projection module of the intraoral scanner will be enabled, such that the image sensor and the projection module can operate normally. When all of the three motion variations are larger than the three first variation thresholds, it means that the intraoral scanner is in an idle state. At this time, at least one of the image sensor and the projection module will be disabled, such that at least one of the image sensor and the projection module stop operating. Accordingly, the invention can reduce power consumption and avoid temperature rise effectively while the intraoral scanner is in an idle state. Furthermore, the invention may utilize the proximity sensor or the blur of image to assist in determining that the intraoral scanner is in an operation state or in an idle state. Moreover, the invention may utilize the magnetic sensor to determine whether the intraoral scanner is placed on the support frame, so as to further determine that the intraoral scanner is in a standby state or in an idle state for switching related component correspondingly, such that the power consumption can be further reduced.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An intraoral scanner comprising:
   an image sensor;
   a projection module;
   a motion sensor sensing three motion variations corresponding to three axes according to a motion state of the intraoral scanner;
   a memory unit storing three first variation thresholds corresponding to the three axes; and
   a processor electrically connected to the image sensor, the projection module, the motion sensor, and the memory unit, the processor determining whether the three motion variations are smaller than or equal to the three first variation thresholds, respectively; when the processor determines that at least one of the three motion variations is smaller than or equal to the three first variation thresholds, the processor enabling the image sensor and the projection module; when the processor determines that all of the three motion variations are larger than the three first variation thresholds, the processor disabling at least one of the image sensor and the projection module.

2. The intraoral scanner of claim 1, adapted to be disposed on a support frame, the support frame comprising a magnetic member, the memory unit storing a voltage threshold, the intraoral scanner further comprising a magnetic sensor and a power supply, the processor being electrically connected to the magnetic sensor and the power supply, the magnetic sensor sensing a magnetic flux of the magnetic member to generate a sensing voltage, the processor determining whether the sensing voltage is larger than or equal to the voltage threshold; when the processor determines that the sensing voltage is larger than or equal to the voltage threshold, the processor enabling the motion sensor; when the processor determines that the sensing voltage is smaller than the voltage threshold, the processor controlling the power supply to supply power to the image sensor and the projection module.

3. The intraoral scanner of claim 2, wherein when the processor determines that the sensing voltage is larger than or equal to the voltage threshold, the processor sets three second variation thresholds corresponding to the three axes according to the three motion variations and stores the three second variation thresholds in the memory unit; the three second variation thresholds are smaller than the three first variation thresholds, respectively; when the processor determines that the sensing voltage is smaller than the voltage threshold and all of the three motion variations are smaller than or equal to the three second variation thresholds, the processor controls the power supply to stop supplying power to the image sensor and the projection module.

4. The intraoral scanner of claim 1, further comprising a proximity sensor, the processor being electrically connected to the proximity sensor, the proximity sensor sensing a current distance between the intraoral scanner and an object, the memory unit storing a distance threshold, the processor determining whether the current distance is smaller than or equal to the distance threshold; when the processor determines that the current distance is smaller than or equal to the distance threshold, the processor enabling the image sensor and the projection module; when the processor determines that the current distance is larger than the distance threshold exceeding a predetermined time period, the processor disabling at least one of the image sensor and the projection module.

5. The intraoral scanner of claim 1, wherein the image sensor senses an image sequence, the memory unit stores a blur threshold, and the processor determines whether a blur of at least one image of the image sequence is larger than or equal to the blur threshold; when the processor determines that the blur of the at least one image is larger than or equal to the blur threshold, the processor disables at least one of the image sensor and the projection module.

6. An intraoral scanning system comprising:
a host device storing three first variation thresholds corresponding to three axes; and
an intraoral scanner communicating with the host device, the intraoral scanner comprising:
an image sensor;
a projection module;
a motion sensor sensing three motion variations corresponding to the three axes according to a motion state of the intraoral scanner; and
a processor electrically connected to the image sensor, the projection module, and the motion sensor;
wherein the host device determines whether the three motion variations are smaller than or equal to the three first variation thresholds, respectively; when the host device determines that at least one of the three motion variations is smaller than or equal to the three first variation thresholds, the host device controls the processor to enable the image sensor and the projection module; when the host device determines that all of the three motion variations are larger than the three first variation thresholds, the host device controls the processor to disable at least one of the image sensor and the projection module.

7. The intraoral scanning system of claim 6, further comprising a support frame, the intraoral scanner being adapted to be disposed on the support frame, the support frame comprising a magnetic member, the host device storing a voltage threshold, the intraoral scanner further comprising a magnetic sensor and a power supply, the processor being electrically connected to the magnetic sensor and the power supply, the magnetic sensor sensing a magnetic flux of the magnetic member to generate a sensing voltage, the host device determining whether the sensing voltage is larger than or equal to the voltage threshold; when the host device determines that the sensing voltage is larger than or equal to the voltage threshold, the host device controlling the processor to enable the motion sensor; when the host device determines that the sensing voltage is smaller than the voltage threshold, the host device controlling the processor to control the power supply to supply power to the image sensor and the projection module.

8. The intraoral scanning system of claim 7, wherein when the host device determines that the sensing voltage is larger than or equal to the voltage threshold, the host device sets three second variation thresholds corresponding to the three axes according to the three motion variations and stores the three second variation thresholds; the three second variation thresholds are smaller than the three first variation thresholds, respectively; when the host device determines that the sensing voltage is smaller than the voltage threshold and all of the three motion variations are smaller than or equal to the three second variation thresholds, the host device controls the processor to control the power supply to stop supplying power to the image sensor and the projection module.

9. The intraoral scanning system of claim 6, wherein the intraoral scanner further comprises a proximity sensor, the processor is electrically connected to the proximity sensor, the proximity sensor senses a current distance between the intraoral scanner and an object, the host device stores a distance threshold, the host device determines whether the current distance is smaller than or equal to the distance threshold; when the host device determines that the current distance is smaller than or equal to the distance threshold, the host device controls the processor to enable the image sensor and the projection module; when the host device determines that the current distance is larger than the distance threshold exceeding a predetermined time period, the host device controls the processor to disable at least one of the image sensor and the projection module.

10. The intraoral scanning system of claim 6, wherein the image sensor senses an image sequence, the host device stores a blur threshold, and the host device determines whether a blur of at least one image of the image sequence is larger than or equal to the blur threshold; when the host device determines that the blur of the at least one image is larger than or equal to the blur threshold, the host device controls the processor to disable at least one of the image sensor and the projection module.

11. A method of controlling an intraoral scanner, the intraoral scanner comprising an image sensor, a projection module, and a motion sensor, the method comprising steps of:
sensing, by the motion sensor, three motion variations corresponding to three axes according to a motion state of the intraoral scanner;
determining whether the three motion variations are smaller than or equal to three first variation thresholds corresponding to the three axes, respectively;
when determining that at least one of the three motion variations is smaller than or equal to the three first variation thresholds, enabling the image sensor and the projection module; and
when determining that all of the three motion variations are larger than the three first variation thresholds, disabling at least one of the image sensor and the projection module.

12. The method of claim 11, wherein the intraoral scanner is adapted to be disposed on a support frame, the support frame comprises a magnetic member, the intraoral scanner further comprises a magnetic sensor and a power supply, the method further comprises steps of:
sensing, by the magnetic sensor, a magnetic flux of the magnetic member to generate a sensing voltage;
determining whether the sensing voltage is larger than or equal to the voltage threshold;
when determining that the sensing voltage is larger than or equal to the voltage threshold, enabling the motion sensor; and
when determining that the sensing voltage is smaller than the voltage threshold, controlling the power supply to supply power to the image sensor and the projection module.

13. The method of claim 12, further comprising steps of:
when determining that the sensing voltage is larger than or equal to the voltage threshold, setting three second variation thresholds corresponding to the three axes according to the three motion variations, wherein the three second variation thresholds are smaller than the three first variation thresholds, respectively; and
when determining that the sensing voltage is smaller than the voltage threshold and all of the three motion variations are smaller than or equal to the three second variation thresholds, controlling the power supply to stop supplying power to the image sensor and the projection module.

14. The method of claim 11, wherein the intraoral scanner further comprises a proximity sensor, the method further comprises steps of:
sensing, by the proximity sensor, a current distance between the intraoral scanner and an object;

determining whether the current distance is smaller than or equal to a distance threshold;

when determining that the current distance is smaller than or equal to the distance threshold, enabling the image sensor and the projection module; and when determining that the current distance is larger than the distance threshold exceeding a predetermined time period, disabling at least one of the image sensor and the projection module.

15. The method of claim 11, further comprising steps of:

sensing, by the image sensor, an image sequence;

determining whether a blur of at least one image of the image sequence is larger than or equal to a blur threshold; and when determining that the blur of the at least one image is larger than or equal to the blur threshold, disabling at least one of the image sensor and the projection module.

* * * * *